Figure 1:
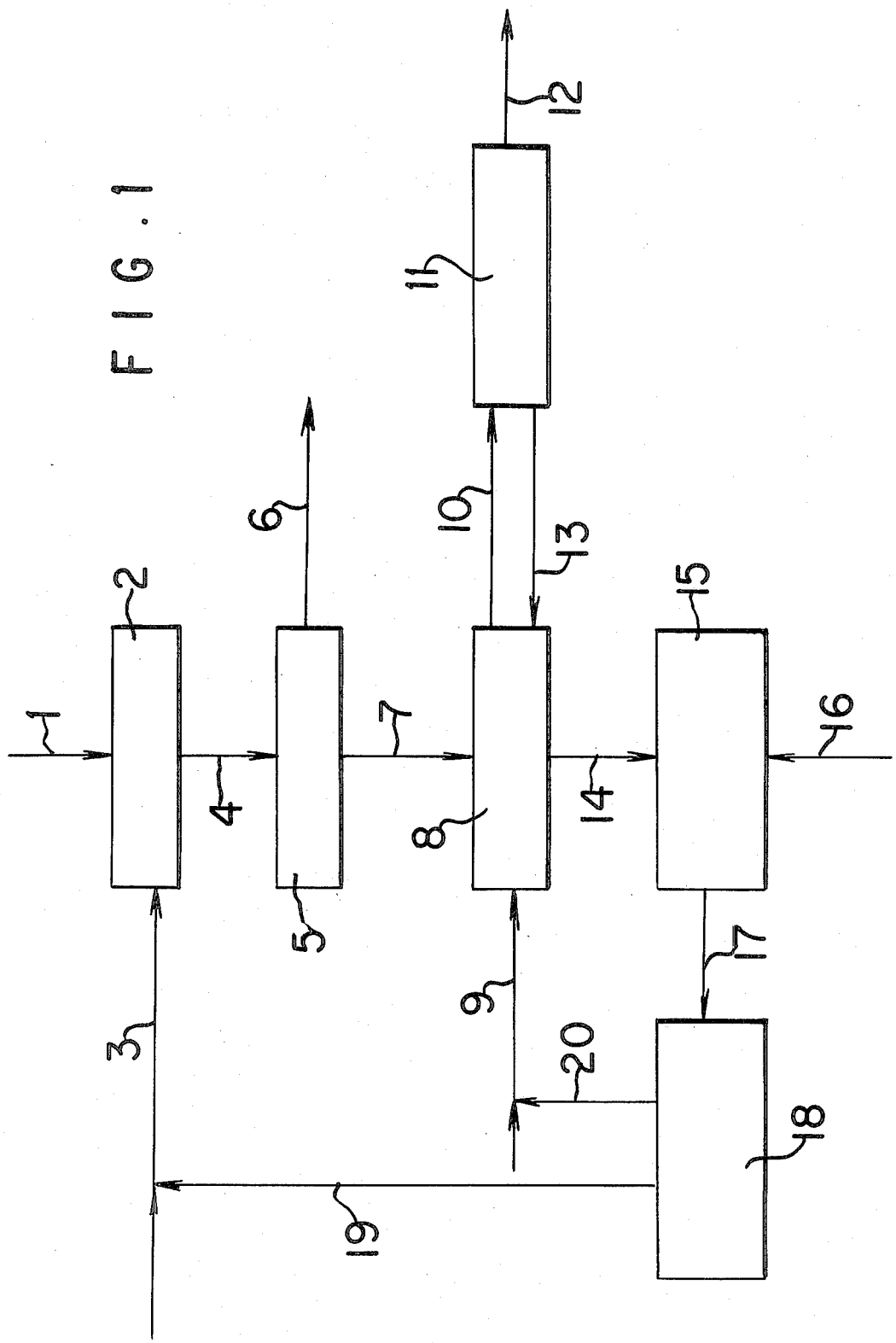

United States Patent [19]

Spaziante et al.

[11] 4,384,999
[45] May 24, 1983

[54] PREPARATION OF ALKYL ISOCYANATES

[76] Inventors: Placido M. Spaziante, Via Zurigo 38, 6900 Lugano, Switzerland; Luigi Giuffre, Via Passo di Fargorida 6, Milano, Italy; Giancarlo Sioli, Via Bismara 10, Cernobbio, Italy; Mirco Fornaroli, Via 4 Novembre, 50, Romentino, Italy

[21] Appl. No.: 195,648

[22] Filed: Oct. 9, 1980

[51] Int. Cl.³ .......................................... C07C 118/02
[52] U.S. Cl. ........................... 260/453 PH; 260/453 P
[58] Field of Search ....................... 260/453 PH, 453 P

[56] References Cited

U.S. PATENT DOCUMENTS 3,644,461  2/1972  Rennells .......................... 260/453 P
4,151,193  4/1979  Crochemore .................... 260/453 P Primary Examiner—Dolph H. Torrence
Attorney, Agent, or Firm—Hammond & Littell, Weissenberger and Muserlian

[57] ABSTRACT

A novel process for the preparation of alkyl isocyanates comprising reacting $COX_2$ and an alkyl amine hydrohalide of the formula $$R\text{-}NH_2.HX \qquad \qquad I$$

wherein R is alkyl of 1 to 3 carbon atoms and X is a halogen either under pressure in an inert organic solvent or under atmospheric pressure in a high boiling organic solvent to form the corresponding alkyl carbamoyl halide, reacting the latter in an organic solvent with an urea of the formula

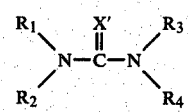

wherein X' is selected from the group consisting of oxygen and sulfur, $R_1$ and $R_3$ are individually selected from the group consisting of alkyl of 1 to 7 carbon atoms, cycloalkyl of 4 to 6 carbon atoms and phenyl and $R_2$ and $R_4$ are individually selected from the group consisting of hydrogen, alkyl of 1 to 7 carbon atoms, cycyloalkyl of 4 to 6 carbon atoms and phenyl to obtain the corresponding alkyl isocyanate.

9 Claims, 2 Drawing Figures

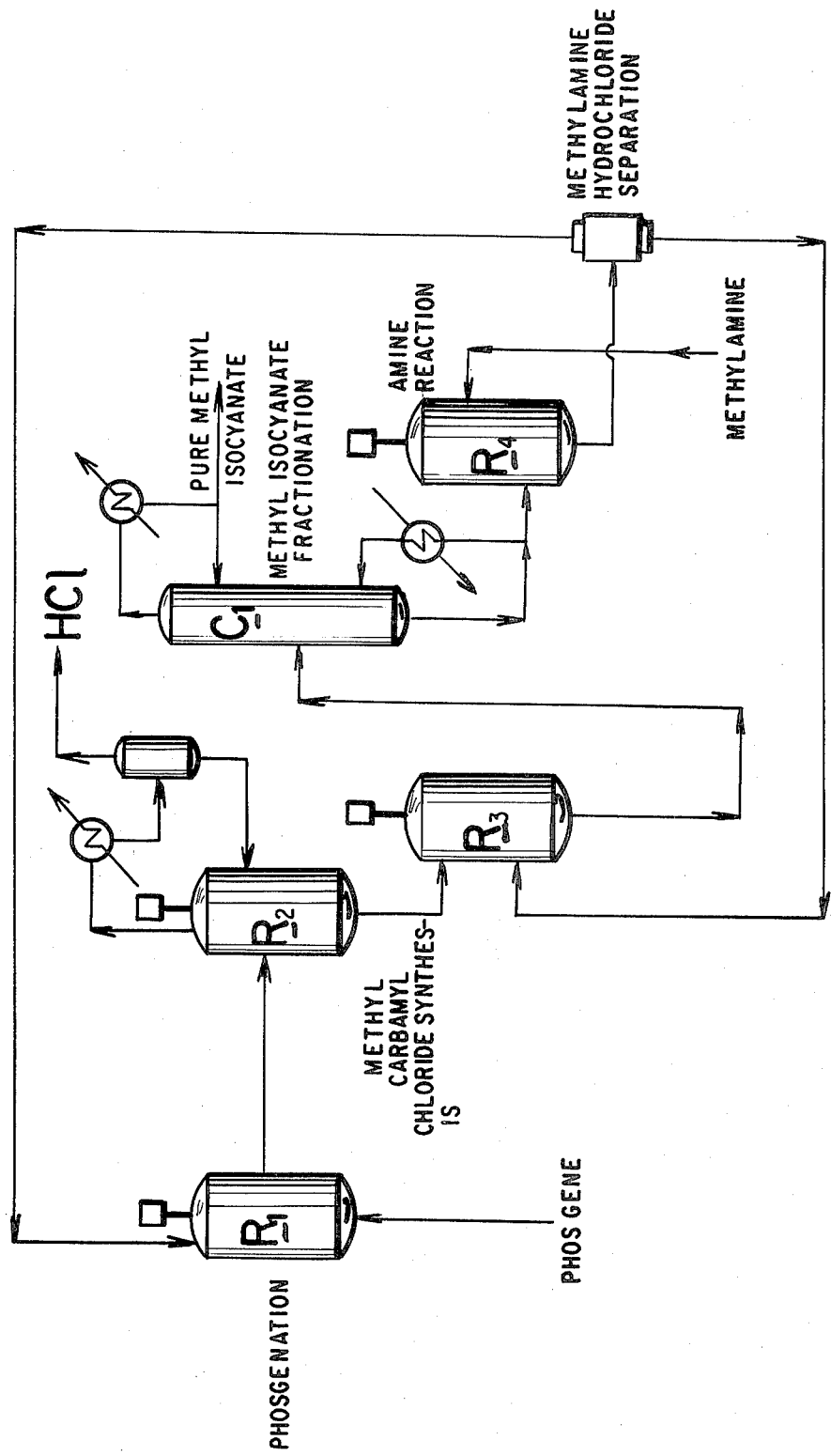

PREPARATION OF ALKYL ISOCYANATES

STATE OF THE ART

Alkyl isocyanates, such as methyl isocyanate, have been prepared by passing through the alkyl carbamyl hydrohalide such as methyl carbamylchloride. Methyl carbamyl chloride has been prepared by reacting in the vapor phase at 275° to 300° C. phosgene and methylamine according to the following reaction scheme.

$$CH_3NH_2 + COCl_2 \longrightarrow CH_3NCO + 2HCl \quad (1)$$

$$CH_3NCO + HCl \longrightarrow CH_3NHCOCl \quad (2)$$

$$CH_3NH_2 + COCl_2 \longrightarrow CH_3NHCOCl + HCl \quad (3)$$

The reaction gases are then cooled to about 50° C. and the gaseous hydrogen chloride is separated from the liquid methyl carbamyl chloride. The cooled reaction products may be absorbed in an organic solvent such as benzene, toluene, chloroform or carbon tetrachloride to obtain a solution or suspension of methylcarbamyl chloride from which hydrogen chloride and excess phosgene can be removed.

Another method of producing methyl carbamyl chloride comprising bubbling phosgene at about 250° C. through molten methylamine hydrochloride or a slurry thereof in a high boiling organic solvent as taught by German Pat. No. 952,086 and Netherlands Pat. No. 65-12169. The reaction is illustrated as follows:

$$CH_3NH_3{}^+Cl^- + COCl_2 \rightarrow CH_3NCO + 3HCl \quad (4)$$

The reaction mixture is then cooled to obtain either molten methylcarbamyl chloride or a solution or suspension thereof in the organic solvent.

The methylcarbamyl hydrochloride may then be converted to hydrogen chloride and methyl isocyanate by three different means. Methylcarbamyl chloride may be reacted with a base such as tertiary amines such as dimethyl-aniline or pyridine or a disubstituted amide to evolve methyl isocyanate in the gaseous phase. The process has the disadvantage that the salt with the base has to be neutralized with a strong base such as sodium hydroxide resulting in a total loss of the hydrogen chloride and involves the expense of the strong base.

A second method comprises reacting methylcarbamyl chloride with compounds having mobile hydrogen atoms such as phenols, monosubstituted sulfonamide, etc. to release hydrogen chloride and the adducts are decomposed at high temperature (U.S. Pat. Nos. 4,003,938 and 4,146,550). This method has the disadvantage of requiring high temperatures and substantial losses of reactants and only moderate yields.

The third method separates methyl isocyanate and hydrogen chloride by fractionation of methylcarbamyl chloride in several columns with optional presence of organic solvents with gradual enrichment of methyl isocyanate solution as described in U.S. Pat. No. 4,082,786 and German Pat. No. 2,703,281. This method has the disadvantage of high operating costs, large capital investment and low yields due to partial polymerization of methyl isocyanate.

OBJECTS OF THE INVENTION

It is an object of the invention to provide an improved process for the production of alkyl isocyanates in an economical manner with good yields.

It is a further object of the invention to provide a process using ureas of formula II as an acid acceptor.

These and other objects and advantages of the invention will become obvious from the following detailed description.

THE INVENTION

The novel process of the invention for the preparation of alkyl isocyanates comprises reacting $COX_2$ and an alkyl amine hydrohalide of the formula $$R-NH_2 \cdot HX \qquad \qquad I$$

wherein R is alkyl of 1 to 3 carbon atoms and X is halogen either under pressure in an inert organic solvent or under atmospheric pressure in a high boiling organic solvent to form the corresponding alkyl carbamoyl halide, reacting the latter in an organic solvent with an ureas of the formula $$\begin{array}{c} R_1 \\ \phantom{R}\diagdown \\ \phantom{R_1R_2}N-\overset{\overset{\displaystyle X}{\|}}{C}-N \\ \phantom{R}\diagup \phantom{RRRR}\diagdown \\ R_2 \phantom{RRRRRRR} R_4 \end{array} \qquad \text{II}$$

wherein X' is selected from the group consisting of oxygen and sulfur, $R_1$ and $R_3$ are individually selected from the group consisting of alkyl of 1 to 7 carbon atoms, cycloalkyl of 4 to 6 carbon atoms and phenyl and $R_2$ and $R_4$ are individually selected from the group consisting of hydrogen, alkyl of 1 to 7 carbon atoms, cycloalkyl of 4 to 6 carbon atoms and phenyl to obtain the corresponding alkyl isocyanate.

The salt of hydrogen halide and the urea of formula II may be reacted with the alkylamine to form the corresponding alkylamine hydrohalide of formula I which may then be recycled to the reaction with phosgene. Preferably, the solvent for this reaction is selected so that the alkylamine hydrohalide is insoluble therein for easy recovery of the product and the resulting solution of the regenerated urea of formula II may be recycled as well.

The said regenerated step is substantially quantitative and the urea is obtained in a substantially pure state. Any urea impurities which may be admixed with the alkylamine hydrochloride will not interfere with the reaction as it will react with phosgene and if it is N,N'-dimethylurea used in methyl isocyanate production, it will react according to the equation.

$$CH_3-NH-\overset{\overset{\displaystyle O}{\|}}{C}-NH-CH_3 + COCl_2 \longrightarrow$$

$$2\ CH_3-NCO + 2HCl$$

When phosgenation is to take place in an inert solvent under pressure, the alkylamine hydrochlorides are suspended in this solvent and the phosgene is then added to the suspension under pressure which causes dissolution to occur. The process of the invention avoids an excess of phosgene and avoids the problems of clogging when a gaseous reaction phase is used. The pressure may vary from 10 to 25 atmospheres and the reaction temperatures may vary from 160° to 200° C., preferably from 170°–180° C.

Alternatively, the alkylamine hydrochlorides are suspended in a high boiling point organic solvent and the phosgene is then added to the suspension. Phosgenation, in this case, takes place under atmospheric pressure and the reaction temperature may vary from 160° to 200° C., preferably between 170°–180° C. Examples of suitable solvents are The organic solvent used in the second step of the process should not react with the urea or alkylamine hydrohalide and preferably has a boiling point at least 15° to 20° C. higher than the boiling point of the alkyl isocyanate for easy separation by fractional distillation. It also should be a good solvent for the urea and preferably for the urea hydrohalide while not dissolving alkylamine hydrohalide. The preferred solvent is chloroform although other inert organic solvents may be used such as dichloromethane, 1,2-dichloroethane, 1,1,2-trichloroethane and other solvents which are able to dissolve the urea of formula II and its hydrohalides.

The alkyl isocyanates are preferably methyl isocyanate, ethyl isocyanate, n-propyl isocyanate and isopropyl isocyanate.

Examples of suitable ureas are N,N'-dimethylurea, N,N-diethylurea, N,N'-diethylurea, N-methyl-N'-ethylurea, N-methyl-N'-butylurea, N-methyl-N'-cyclohexylurea and N-methyl-N'-phenylurea. The alkyl groups are preferably methyl, ethyl, propyl, isopropyl, n-butyl, sec-butyl or tert.-butyl.

REFERRING NOW TO THE DRAWINGS

FIG. 1 illustrates a preferred continuous process for the production of methyl isocyanate in which phosgene is reacted under pressure below 200° C. with a suspension of methylamine hydrochloride in a suitable organic solvent. The reaction mixture is then a homogeneous organic solution of methyl isocyanate and a gaseous phase containing phosgene, the hydrogen chloride produced and a part of methyl isocyanate and the mixture is then flashed at atmospheric pressure to obtain a two phase suspension of methyl carbamyl chloride from which the hydrogenchloride is easily removed.

This process is illustrated in FIG. 1 wherein phosgene and a suspension of methylamine hydrochloride in an organic solvent are added to a stirred reactor R-1 and the mixture is then passed to second stirred reactor R-2 wherein methyl carbamyl chloride is formed and gaseous hydrogen chloride is removed. The resulting slurry of methyl carbamyl chloride is transferred to reactor R-3 wherein it is reacted with N,N'-dimethylurea to obtain a single phase solution containing methyl isocyanate. The said solution is passed through fractionation column C-1 to recover methyl isocyanate at the top thereof and the mixture of N,N'-dimethylurea solution and hydrogen chloride is removed from the bottom of C-1. The latter mixture is passed to reactor R-4 to react with methylamine and the resulting suspension of methylamine hydrochloride and solvent is separated. The methylamine hydrochloride solid is suspended in an organic solvent and is recycled to reactor R-1. The filtrate containing free hydrogen chloride and N,N'-dimethylurea is recycled to reactor R-3 whereby no loss of reactant occurs and there are no waste disposal problems.

FIG. 2 illustrates the same basic process as FIG. 1 except that phosgene is reacted in a high boiling organic solvent at the preferred temperatures of 170° to 180° C. The phosgenation solvent is removed from the reaction mixture and is replaced with a suitable solvent for the synthesis of methyl carbamyl chloride which results in a carry over of solvent.

In FIG. 2, a process is illustrated for the production of 10,000 million tons per year of methyl isocyanate. Phosgene is introduced by line 1 into furnace 2 simultaneously with a suspension of methylamine hydrochloride in an organic solvent by line 3 and the resulting gaseous phase of methylcarbamoyl chloride and hydrogen chloride is passed by line 4 to cooler 5 wherein where hydrogen chloride is recovered by line 6. Methylcarbamoyl chloride is dissolved in an organic solvent and passed by line 7 to reactor 8 wherein it is reacted with a chloroform solution of N,N'-dimethylurea introduced by line 9.

In the following examples there are described several preferred embodiments to illustrate the invention. However, it should be understood that the invention is not intended to be limited to the specific embodiments.

EXAMPLE 1

67 g of methylamine hydrochloride and 268 g of chloroform were introduced at room temperature into a one liter stainless steel reactor which was then closed and heated by diathermic oil circulation in the reaction jacket. When the temperature reached 175° C., the pressure was 15 atmospheres gauge and then a solution of 500 g of phosgene per liter of chloroform was added to the reactor at the rate of 5.6 ml/min with a stainless steel micro pump. The volatile reaction products were removed from the reactor through a preset pressure release valve and were then condensed at 0° C. whereby the majority of the hydrogen chloride is separated. The phosgene solution was added to the reactor over 42 minutes to introduce a total of 236 g of phosgene for a molar ratio of phosgene to methylamine hydrochloride of 1.2. Analysis of the condensate showed 83.2 g (89% yield based on methylamine hydrochloride) of methyl carbamyl chloride.

EXAMPLE 2

A suspension of 67 g of methyl carbamyl chloride in 300 ml of o-dichloro-benzene was added with stirring to a jacketed 500 ml glass reactor and the mixture was heated to 175° C. by circulation of diathermic oil in the reactor jacket. Then, a solution of 500 g of phosgene per liter of o-dichloro-benzene was introduced into the reactor at a rate of 3.2 ml/min. for 40 minutes and the volatile products were condensed at 0° C. to obtain 45.3 g of methyl carbamyl chloride for a 75% yield based on phosgene.

EXAMPLE 3

5.21 g (40.0 mmoles) of N-methyl-N'-butyl-urea and 50 ml of anhydrous methylene chloride were added to a 150 ml jacketed reactor equipped with a claisen condenser, a magnetic stirrer and a funnel and then 2.10 g (22.0 mmoles) of 98% methylcarbamoyl chloride were added thereto with stirring while warm water was circulated in the reactor jacket. Methyl isocyanate with a boiling poing of 39° C. and methylene chloride (b.p.=40° C.) were distilled and collected at −20° C. in a receiver. Methylene chloride was constantly added during the distillation to keep the volume constant and after 50 ml of distillate were collected, the distillation was stopped. The concentration of N-methyl-N'-butylurea in methylene chloride was 7.32% by weight and the ratio of N-methyl-N'-butyl-urea to methylcarbamoyl chloride was 1.82. Analysis of the collected methyl isocyanate and N-methyl-N'-butyl-urea hydrochloride in the reaction vessel showed a yield of 90.5% of methyl isocyanate.

EXAMPLE 4

8.99 g (100.1 mmoles) of 98% N,N-dimethyl-urea and 40 ml of chloroform (b.p.=61° C.) were added to the apparatus of Example 3 and the mixture was heated to reflux with stirring. A suspension of 4.74 g (50.4 mmoles) of 99.3% methylcarbamoyl chloride in 40 ml of chloroform were added over 30 minutes to the refluxing mixture and then methyl isocyanate was distilled while adding 40 ml of chloroform to keep the volume constant. The concentration of N,N-dimethylurea was 12.94% by weight and the ratio of methylcarbamoyl chloride to N,N-dimethylurea was 1:1.99. The collected distillate was 80 ml containing 49.1 mmoles (97.42% yield) of methyl isocyanate free of chloride ions.

EXAMPLE 5

A mixture of 17.71 g (197 mmoles) of 98% N,N-methylurea and 50 ml of chloroform in the apparatus of Example 3 was refluxed with stirring while adding over 30 minutes a suspension of 15.43 g (164.2 mmoles) of 99.5% methylcarbamoyl chloride in 50 ml of chloroform. The mixture was distilled while keeping the volume constant by adding 50 ml of chloroform to the mixture. The concentration of N,N-dimethylurea was 18.97% by weight and the ratio of methylcarbamoyl chloride to N,N-dimethyl-urea was 1:1.20. The 100 ml of collected distillate contained 159.1 mmoles (96.89% yield) of methyl isocyanate free of chloride ions.

EXAMPLE 6

A solution of 10.91 g (191.3 mmoles) of 98% N,N-dimethyl-urea in 50 ml of chloroform was refluxed with stirring in the apparatus of Example 3 while 9.37 g of melted methylcarbamoyl chloride in a jacketed burette maintained at 50° C. were added dropwise over 20 minutes. Methyl isocyanate was distilled from the mixture while adding 100 ml of chloroform to keep the volume of the mixture constant. The concentration of N,N-dimethylurea was 18.31% by weight and the ratio of methylcarbamoyl chloride to N,N-dimethylurea was 1:1.22. The distillate contained 95.7 mmoles (96% yield) of methyl isocyanate.

Excess gaseous methylamine was bubbled through the reactor solution at 40° C. which caused a white precipitate of methylamine hydrochloride to form. The mixture was filtered and the crystals were washed with 50 ml of chloroform and was dried to obtain 6.61 g (97.9 mmoles) of the said hydrochloride which was a yield of 98.19% with respect to the chloride ion content in methylcarbamoyl chloride.

EXAMPLE 7

A mixture of 19.35 g (215.2 mmoles) of N,N-dimethylurea and 50 ml of chloroform in the apparatus of Example 3 was refluxed with stirring while adding thereto a suspension of 19.08 g (203 mmoles) of 99.5% methycarbamoyl chloride in 50 ml of chloroform. The concentration of N,N-dimethyl-urea was 20.69% by weight and the ratio of methylcarbamoyl chloride to N,N-dimethyl-urea was 1:1.06. Methyl isocyanate was distilled while 50 ml of chloroform were added to the mixture and the 100 ml of distillate contained 189.4 mmoles (96.7% yield) of methyl isocyanate. 7.1 mmoles of methylcarbamoyl chloride were recovered.

EXAMPLE 8

A mixture of 17.84 g (148.9 mmoles) of 97% tetramethyl urea in 50 ml of chloroform in the apparatus of Example 3 was refluxed with stirring while adding dropwise thereto a suspension of 11.57 g (129.1 mmoles) of 99.5% methylcarbamoyl chloride in 50 ml of chloroform over 20 minutes. The concentration of tetramethylurea was 18.9% by weight and the molar ratio of methylcarbamoyl chloride to tetramethylurea was 1:1.21. Methyl isocyanate was distilled from the mixture while 50 ml of chloroform were added thereto and the distillate contained 118.4 mmoles (96.2% yield) of methyl isocyanate free of chloride ions.

EXAMPLE 9

A solution of 14.84 g (165 mmoles) of 98% N,N-methylurea in 50 ml of 1,1,2-trichloroethylene (b.p.=113.8° C.) in the apparatus of Example 3 was refluxed with stirring while 17.3 g (139.8 mmoles) of 98.2% N-propylcarbamoyl chloride were added thereto. The concentration of N,N-dimethylurea was 16.8% by weight and the molar ratio of N-propylcarbamoyl chloride to N,N-dimethylurea was 1:1.18. A white precipitate of N,N-dimethylurea hydrochloride formed in the reaction vessel while 100 ml of distillate was collected containing 131.3 mmoles (93.9% yield) of N-propyl isocyanate free of chloride ions.

Various modifications of the processes of the invention may be made without departing from the spirit or scope thereof and it is to be understood that the invention is intended to be limited only as defined in the appended claims.

We claim:

1. A process for the production of alkyl isocyanates comprising reacting $COX_2$ and an alkyl amine hydrohalide of the formula

wherein R is alkyl of 1 to 3 carbon atoms and X is a halogen either under pressure in an inert organic solvent or under atmospheric pressure in a high boiling organic solvent to form the corresponding alkylcarbamoyl halide, reacting the latter in an organic solvent with an urea of the formula

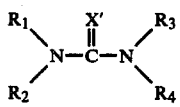

wherein X' is selected from the group consisting of oxygen and sulfur, $R_1$ and $R_3$ are individually selected from the group consisting of alkyl of 1 to 7 carbon atoms, cycloalkyl of 4 to 6 carbon atoms and phenyl and $R_2$ and $R_4$ are hydrogen to obtain the corresponding alkyl isocyanates and the urea hydrohalide and reacting the latter with additional alkylamine to form the alkylamine hydrohalide which is recycled.

2. The process of claim 1 wherein $COX_2$ is phosgene.

3. The process of claim 1 wherein the urea is selected from the group consisting of N,N'-dimethylurea, N,N'-diethylurea, N,N'-dimethylthiourea, N-methyl-N'- ethylurea, N-methyl-N'-butylurea, N-methyl-N'-cyclohexylurea and N-methyl-N'-phenylurea.

4. The process of claim 1 wherein the urea is N,N'-dimethylurea.

5. The process of claim 1 wherein the solvent in the second step is chloroform.

6. The process of claim 1 wherein phosgene is reacted at atmospheric pressure in a high boiling organic solvent.

7. The process of claim 1 wherein phosgene is reacted under pressure in an inert organic solvent.

8. The process of claim 7 wherein the solvent is chloroform.

9. The process of claim 1 wherein the organic solvent for the reaction with the urea is one in which the alkylamine hydrohalide is insoluble.

* * * * *